(12) United States Patent
Wiggins et al.

(10) Patent No.: US 8,867,764 B1
(45) Date of Patent: Oct. 21, 2014

(54) CALIBRATED HEARING AID TUNING APPLIANCE

(71) Applicants: Dan Wiggins, Edmonds, WA (US); Don Bowie, Burien, WA (US)

(72) Inventors: Dan Wiggins, Edmonds, WA (US); Don Bowie, Burien, WA (US)

(73) Assignee: Bowie-Wiggins LLC, Burien, WA (US)

( * ) Notice: Subject to any disclaimer, the term of this patent is extended or adjusted under 35 U.S.C. 154(b) by 0 days.

(21) Appl. No.: 13/889,217

(22) Filed: May 7, 2013

Related U.S. Application Data

(63) Continuation of application No. 12/760,435, filed on Apr. 14, 2010, now Pat. No. 8,437,486.

(60) Provisional application No. 61/169,242, filed on Apr. 14, 2009.

(51) Int. Cl.
*H04R 25/04* (2006.01)
*H04R 25/02* (2006.01)
*H04R 25/00* (2006.01)

(52) U.S. Cl.
CPC .................... *H04R 25/305* (2013.01)
USPC .............. 381/314; 381/316; 381/320; 381/60

(58) Field of Classification Search
USPC ......... 381/314, 316, 320, 321, 323, 328, 312, 381/23.1, 60
See application file for complete search history.

(56) References Cited

U.S. PATENT DOCUMENTS

| | | | | |
|---|---|---|---|---|
| 4,548,082 A * | 10/1985 | Engebretson et al. | .......... | 73/585 |
| 5,197,332 A * | 3/1993 | Shennib | .......... | 73/585 |
| 5,210,803 A * | 5/1993 | Martin et al. | .......... | 381/315 |
| 5,226,086 A * | 7/1993 | Platt | .......... | 381/58 |
| 5,604,812 A * | 2/1997 | Meyer | .......... | 381/314 |
| 5,608,803 A * | 3/1997 | Magotra et al. | .......... | 381/314 |
| 5,626,629 A * | 5/1997 | Faltys et al. | .......... | 607/57 |
| 5,710,819 A * | 1/1998 | Tøpholm et al. | .......... | 381/316 |
| 5,910,997 A * | 6/1999 | Ishige et al. | .......... | 381/314 |
| 6,035,050 A * | 3/2000 | Weinfurtner et al. | .......... | 381/313 |
| 6,058,197 A * | 5/2000 | Delage | .......... | 381/314 |
| 6,229,900 B1 * | 5/2001 | Leenen | .......... | 381/314 |
| 6,366,863 B1 * | 4/2002 | Bye et al. | .......... | 702/57 |
| 6,424,722 B1 * | 7/2002 | Hagen et al. | .......... | 381/314 |
| 6,574,340 B1 * | 6/2003 | Bindner et al. | .......... | 381/60 |
| 6,674,867 B2 * | 1/2004 | Basseas | .......... | 381/314 |
| 7,650,005 B2 * | 1/2010 | Chalupper | .......... | 381/320 |
| 7,787,647 B2 * | 8/2010 | Hagen et al. | .......... | 381/314 |
| 7,945,065 B2 * | 5/2011 | Menzl et al. | .......... | 381/314 |
| 8,005,246 B2 * | 8/2011 | Ribic | .......... | 381/316 |
| 8,437,486 B2 * | 5/2013 | Wiggins et al. | .......... | 381/314 |
| 2001/0033664 A1 * | 10/2001 | Poux et al. | .......... | 381/60 |
| 2005/0069163 A1 * | 3/2005 | O'Brien | .......... | 381/314 |

(Continued)

*Primary Examiner* — Edgardo San Martin

(74) *Attorney, Agent, or Firm* — ÆON Law; Adam L. K. Philipp

(57) ABSTRACT

A hearing aid can be tuned while worn by a user according to a heuristic method, including select an adjustable parameter and an stimulus having audio energy characteristics related to the adjustable parameter. The stimulus is played via a calibrated audio output device and amplified by the hearing aid. After selecting a user perception query associated with the adjustable parameter, feedback is obtained from the user indicating that the stimulus was not perceived neutrally. A perceptual adjustment curve and a threshold curve are determined according to the user feedback, and an estimated perception curve that estimates the user's perception of the stimulus is determined. When at least a portion of the estimated perception curve exceeds a threshold curve, the hearing aid is programmed according to at least one adjustment value determined according to the user feedback value.

20 Claims, 11 Drawing Sheets

(56) References Cited

U.S. PATENT DOCUMENTS

| | | | |
|---|---|---|---|
| 2005/0196002 A1* | 9/2005 | Hagen et al. | 381/314 |
| 2008/0056518 A1* | 3/2008 | Burrows et al. | 381/314 |
| 2008/0085023 A1* | 4/2008 | Kulkarni et al. | 381/320 |
| 2010/0272297 A1* | 10/2010 | Boretzki | 381/312 |
| 2010/0303269 A1* | 12/2010 | Baechler | 381/321 |
| 2011/0002490 A1* | 1/2011 | Zukic | 381/314 |
| 2011/0051963 A1* | 3/2011 | Barthel et al. | 381/314 |
| 2011/0188682 A1* | 8/2011 | Menzl et al. | 381/314 |
| 2011/0200214 A1* | 8/2011 | Knox et al. | 381/314 |
| 2012/0140937 A1* | 6/2012 | Poe et al. | 381/60 |

* cited by examiner

CALIBRATED HEARING AID TUNING APPLIANCE

FIELD

The present disclosure relates to hearing aids, and more particularly to tuning hearing aids via a heuristic tuning routine.

BACKGROUND

At some point in their lives, many people may experience a full or partial decrease in their ability to detect or understand some or all sounds, i.e., a hearing impairment. For many such hard of hearing individuals, the degree of hearing impairment varies by sound frequency. For example, many hard of hearing individuals may have little or no impairment at low sound frequencies, but varying degrees of impairment at higher frequencies. Loss of the ability to understand speech is generally regarded as one of the more detrimental aspects of hearing impairment. The frequency range from about 100 Hz-8 kHz is generally regarded as being the most important for being able to understand speech.

In some cases, certain groups of hard of hearing individuals may share certain general characteristics. For example, statistical thresholds of hearing have been developed for men and women of various ages. However, most individuals have a distinct pattern of impairment that may vary from the statistical thresholds. Consequently, devices that are intended to compensate for an individual's personal hearing impairment often perform better when they are matched to the individual's distinct pattern of impairment.

Many hearing aids include one or more adjustable audio-processing circuits and/or routines. For example, hearing aids commonly include one or more equalization filters and/or amplifiers that may be used to selectively boost or cut various portions of the audible frequency spectrum. In addition, many hearing aids also include other adjustable audio-processing circuits and/or routines, such as gain controls, limiters, compressors, and the like. By adjusting a hearing aid's audio-processing parameters, a hearing aid can often be "tuned" to compensate for an individual's distinct pattern of impairment.

Currently, hearing aids are generally tuned by an auditory healthcare professional, often in a clinical setting. As part of the tuning process, an audiogram (a standardized plot representing the individual's hearing threshold) may be created, generally by performing a "pure tone audiometry" hearing test. Pure tone audiometry hearing tests usually involve presenting pure tones at varying frequencies and levels to an individual wearing calibrated headphones in a sound-controlled environment. The resulting audiogram may provide a starting point for tuning a hearing aid, but it is generally regarded that pure tone audiometry may not accurately measure the full extent of an individual's hearing impairment. For example, pure tone audiometry may not be able to accurately measure the effect of "dead regions" in an individual's basilar membrane. In addition, pure tone audiometry may not measure various factors that are important to speech intelligibility.

Consequently, a further step in tuning a hearing aid generally includes assessing speech intelligibility, often by asking the hearing aid wearer to subjectively evaluate spoken words and/or phrases. Often, the auditory healthcare professional will use his or her own voice as an intelligibility test signal, speaking words or phrases and asking the hearing aid wearer to evaluate the spoken words or phrases. In many cases, the spoken words may include words selected from several pairs of words that differ only by an initial, final, or intervocalic consonant. The auditory healthcare professional may then use the individual's responses to adjust various hearing aid audio-processing parameters.

However, this approach to speech intelligibility tuning may have drawbacks. For example, it may be difficult to achieve consistent results from tuning session to tuning session. In many cases, a hearing aid may need to be tuned multiple times, often over a period of days or weeks, before the wearer finds its performance acceptable. In many cases, the auditory healthcare professional's voice may change slightly or significantly from session to session (e.g., the professional's voice may be altered when he or she has a cold), so it may be difficult compare results from session to session. In other cases, an auditory healthcare professional may retire or move, in which case, subsequent speech intelligibility evaluations may be based on a completely different test signal.

DESCRIPTION

Figure 1:
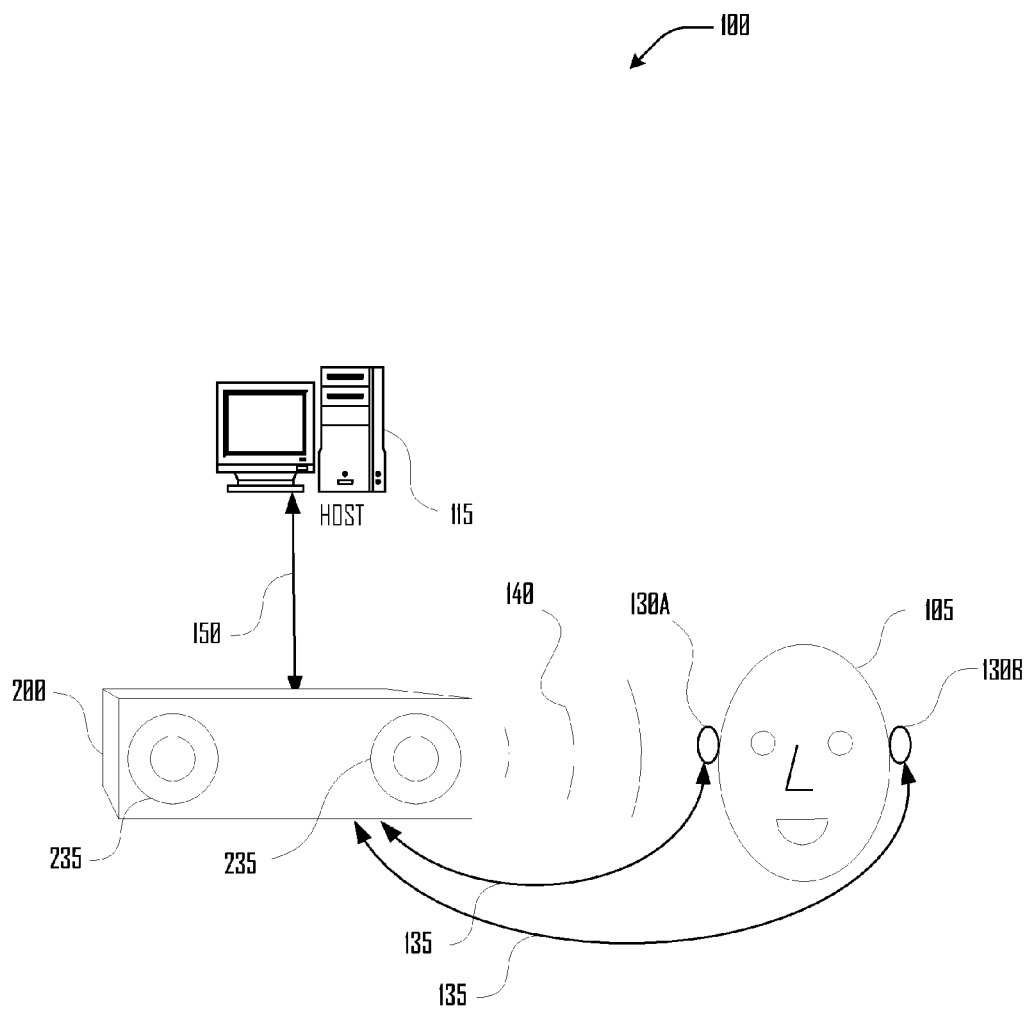
FIG. 1 is a system diagram of a calibrated tuning appliance, a host device, and hearing aids in accordance with one embodiment.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications, and equivalents. In alternate embodiments, additional devices, or combinations of illustrated devices, may be added to, or combined, without limiting the scope to the embodiments disclosed herein.

Various aspects of the illustrative embodiments will be described using terms commonly employed by those skilled in the art to convey the substance of their work to others skilled in the art. However, the embodiments described herein may be practiced with only some of the described aspects. For purposes of explanation, specific numbers, materials, and configurations may be set forth to provide a thorough understanding of the illustrative embodiments. However, the embodiments described herein may be practiced without the specific details. In other instances, well-known features are omitted or simplified in order not to obscure the illustrative embodiments.

Further, various operations and/or communications may be described as multiple discrete operations and/or communications, in turn, in a manner that may be helpful in understanding the embodiments described herein; however, the order of description should not be construed as to imply that these operations and/or communications are necessarily order dependent. In particular, these operations and/or communications need not be performed in the order of presentation.

The phrase "in one embodiment" is used repeatedly. The phrase generally does not refer to the same embodiment; however, it may. The terms "comprising," "having" and "including" are synonymous, unless the context dictates otherwise.

FIG. 1 is a system diagram of a calibrated tuning appliance 200, a host device 115, and hearing aids 130A-B in accordance with one embodiment. Using various embodiments of such a system 100, a hearing aid wearer 105 may be able to tune his or her own hearing aid or hearing aids 130A-B via heuristic tuning routine 500 (see FIGS. 2 and 5, discussed below) and sound waves 140 produced by calibrated electroacoustic transducers 235. In one embodiment, calibrated tuning appliance 200 communicates with a host 115, via a host connection 150, and one or more hearing aids 130A-B, via one or more hearing aid connections 135. Although calibrated tuning appliance 200 and its associated tuning routines 500 may be utilized by a hearing aid wearer 105 to tune his or her own hearing aids 130A-B, calibrated tuning appliance 200 may also be utilized by a auditory healthcare professional to provide a consistent tuning experience to one or more hearing aid wearers 105.

In the exemplary embodiment, calibrated tuning appliance 200 comprises a single enclosure, but in other embodiments, calibrated tuning appliance 200 may comprise one or more separate enclosure. For example, in one embodiment, electroacoustic transducers 235 may be housed in one or more separate enclosures.

In various embodiments, host 115 may comprise a personal computer, laptop, set top box, mobile device, game console, and/or other computing device having a display capability and user-input capability. In alternate embodiments, calibrated tuning appliance 200 may include its own display and/or input device. In still further embodiments, host 115 may comprise a display and/or an input device, but calibrated tuning appliance 200 may use its own internal processor. In some embodiments, calibrated tuning appliance 200 and host 115 may be combined into a single device.

Figure 2:
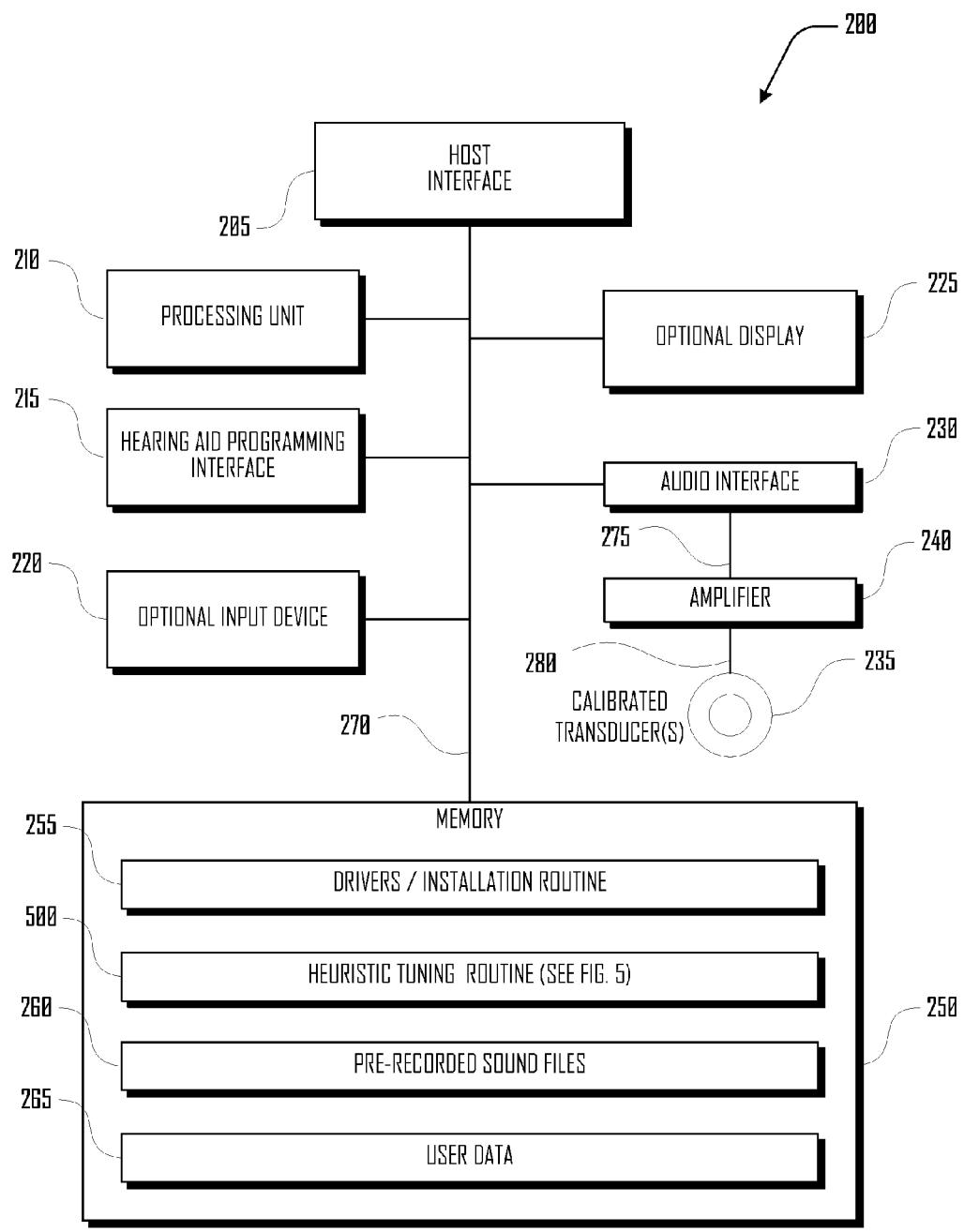
FIG. 2 is a block diagram of a calibrated tuning appliance in accordance with one embodiment.

FIG. 2 illustrates a calibrated tuning appliance 200 in accordance with one embodiment. In one embodiment, calibrated tuning appliance 200 includes a host interface 205, processing unit 210, hearing aid programming interface 215, optional input device 220, optional display 225, an audio interface 230, and a memory 250, all connected to a bus 270.

In one embodiment, host interface 205 comprises a wired serial or parallel data interface, such as Universal Serial Bus ("USB"), IEEE 1394, and the like. In other embodiments, host interface 205 may comprise a wireless data interface, such as an Infrared Data Association ("IrDA") interface, Bluetooth, wireless USB, and the like. In still other embodiments, host interface 205 may comprise a wired or wireless network connection, such as IEEE 802.3 (i.e., Ethernet), IEEE 802.11 (i.e., Wi-Fi), and the like.

In one embodiment, processing unit 210 may comprise a processor sufficient to control communications between host interface 205, memory 250, and audio interface 230 and optional interfaces 220 and 225. In other embodiments, processing unit 210 may comprise a more powerful central processing unit, such as those found in personal computers, laptops, mobile devices, and the like.

In one embodiment, hearing aid programming interface 215 comprises a data interface coupled to calibrated tuning appliance 200 via a fixed or removable coupler, and coupled to one or more hearing aid earpieces 130A-B via a removable coupler. In one embodiment, hearing aid programming interface 215 comprises a wired data connection. In other embodiments, hearing aid programming interface 215 may comprise a wireless data connection. In one embodiment, hearing aid programming interface 215 is coupled to one or more hearing aid earpieces 130A-B via a magnetic-inductive data coupler, as described in U.S. patent application Ser. No. 12/760,423 (now U.S. Pat. No. 8,363,872) entitled "MAGNETIC EARPIECE COUPLING SYSTEM," with inventors Daniel Wiggins and Donald Bowie, which is hereby fully incorporated by reference.

Optional input device 220, if present, may include a pointing device, such as a mouse, track pad, track ball, touch screen, and the like. In other embodiments, optional input device 220, if present, may include voice input capacity. Similarly, optional display 225, if present, may include an optical display screen and/or a voice interface.

In various embodiments, memory 250 may comprise volatile random access memory, such as dynamic random access memory; non-volatile memory, such as read-only memory ("ROM") and/or flash memory; non-volatile storage devices, such as a hard disk drive, optical disk, and/or holographic data storage; and/or other memory device. Memory 250 may include internal and/or external memory devices. In one embodiment, memory 250 includes software 255 used to interface with and/or be controlled by a host 115, including one or more device drivers 255 and/or an installation routine.

In one embodiment, drivers/installation routine 255 may include "auto-run" or other automatic installation routines such that in many cases, a hearing aid wearer 105 may be able to initiate a tuning session simply by connecting the calibrated tuning appliance 200 to a host 115. For example, when connected to a host 115, a calibrated tuning appliance 200 may initially identify itself as a common mass storage device, such as a CD-ROM, disk image, flash drive, and the like. Many current operating systems allow such mass storage devices to provide an executable, script, file, or the like that will be automatically opened, launched, and/or executed when a mass storage device mounts and/or is connected. Using such functionality, in one embodiment, calibrated tuning appliance 200 may cause the host 115 operating system to automatically install a device driver to enable the host 115 operating system to interact in a meaningful manner with calibrated tuning appliance 200.

Furthermore, in various embodiments, once host 115 is able to meaningfully interact with calibrated tuning appliance 200, heuristic tuning routine 500 may automatically launch. The operations of heuristic tuning routine 500 are set forth in greater detail in FIGS. 4-11 and associated description (below) and in U.S. patent application Ser. No. 12/760,431 entitled "HEARING AID TUNING METHOD", with inventors Daniel Wiggins and Donald Bowie. Each of the above-referenced applications is hereby fully incorporated by reference.

In some embodiments, heuristic tuning routine 500 may also automatically utilize a network connection on host 115 to provide automatic self-update functionality, such that users may have access to the most recent software version without requiring the user to take any explicit steps to maintain his or her installation of the heuristic tuning routine 500.

In various embodiments, heuristic tuning routine 500 may provide a platform-neutral user interface. For example, in one embodiment, heuristic tuning routine 500 may be implemented as a local or remote web page or web site that provides a user interface via a web browser on host 115. In other embodiments, heuristic tuning routine 500 may be implemented as an interpreted script, interpreted byte code, compiled byte code, virtual machine instructions, and the like. For example, in various embodiments, heuristic tuning routine 500 may be implemented in Java, Flash, and/or other cross-platform development platform. In still further embodiments, heuristic tuning routine 500 may be implemented as one or more conventional single-platform executables.

Thus, in accordance with various embodiments, calibrated tuning appliance 200 may provide an entirely self-contained, "plug and play," solution, in which a user is not required to use or retain a separate software installation disc nor to even download software via the Internet or other data network.

In various embodiments, memory 250 may also include one or more pre-recorded sound files 260. As used herein, the term "sound file" refers to an electronic file containing data from which an audio signal may be constructed. For example, a "sound file" may include pulse-code modulation ("PCM") data, compressed or uncompressed, stored in various file formats, including Audio Interchange File Format ("AIFF"), Waveform audio format ("WAV"), and the like. A sound file may also include lossy compressed audio data, such as audio data encoded in MPEG-1 Audio Layer 3 ("MP3") format, Advanced Audio Coding ("AAC") format, Vorbis format, and the like.

In some embodiments, a sound file may also include data from which an audio signal may be constructed according to one or more synthesis routines. For example, in one embodiment, an audio file may include linear predictive coding ("LPC") coefficients for synthesizing a speech audio signal or other audio signal. An audio file may also include data and/or routines to produce audio signals other than speech, including pure tones, tone combinations, noise, music, and the like.

In one embodiment, some or all pre-recorded sound files 260 may be based on standardized sound files used for subjective evaluation of telecommunication systems, such as sound files prepared in accordance with TIA-920 standard promulgated by the U.S. Telecommunications Industry Association ("TIA"). In some embodiments, pre-recorded sound files 260 may comprise other recordings of speech, including recordings of words, word pairs, phrases, and the like recorded by one or more speakers having determined vocal characteristics (e.g., low male voice, high female voice, and the like). In some embodiments, pre-recorded sound files 260 may further comprise other recorded material, including musical recordings (or excerpts thereof), soundtrack recordings (or excerpts thereof), pure tone recordings, noise recordings (e.g., white noise, pink noise, and other forms of noise having predetermined frequency spectra), and the like.

Memory 250 may also include user data 265. In some embodiments, some or all of memory 250 may be accessible by a user as, for example, a data volume mounted on host 115. In such embodiments, a user may store arbitrary data in memory 250. In other embodiments, a user may not have direct access to memory 250, but heuristic tuning routine 500 may securely store data associated with a user in user data 265. For example, heuristic tuning routine 500 may store in user data 265 user preferences, user hearing aid tuning settings, user hearing aid presets, past user hearing aid tuning settings, and the like. In some embodiments, a user may be able to provide custom-recorded sound files for use with heuristic tuning routine 500, in which case user data 265 may also include one or more custom-recorded sound files. In some such embodiments, calibrated tuning appliance 200 may further comprise a microphone and/or other audio input circuitry.

Audio interface 230 is further connected via an audio bus 275 to amplification circuitry 240 and via at least one amplified audio bus 280, to one or more calibrated electro-acoustic transducers 235. In one embodiment, audio interface 230 comprises a digital-to-analog converter ("DAC"). In other embodiments, a DAC may be included elsewhere in the audio chain, including audio interface 230 through calibrated transducer(s) 235. In various embodiments, amplification circuitry 240, amplified audio bus 280, and one or more calibrated electro-acoustic transducers 235 may be housed in one or more separate enclosures. In one embodiment, amplification circuitry may comprise a Class D (or "switching") amplifier. In other embodiments, other classes of amplification may be utilized, including Classes A, B, A/B, and the like.

In one embodiment, calibrated tuning appliance 200 may include one or more calibrated electro-acoustic transducers 235 capable of transducing electrical signals into sound waves 140 according to one or more predetermined performance parameters. For example, in one embodiment, electro-acoustic transducers 235 may be capable of producing sound waves from 150 Hz-8 kHz at 85-90 dB (SPL) (measured at 1 meter) with no more than +/−3 dB of deviation in frequency response and no more than 3% total harmonic distortion ("THD"). In one embodiment, a calibrated electro-acoustic transducer 235 may comprise a single wide-range transducer between approximately 1-3 inches in diameter. In other embodiments, a calibrated electro-acoustic transducer 235 may comprise one or more individual transducers of varying sizes. For example, in one embodiment, electro-acoustic transducer 235 may comprise a low-frequency transducer, a high-frequency transducer, and an analog and/or digital frequency-dividing network.

In some embodiments, calibrated tuning appliance 200 may employ analog and/or digital response shaping networks to enable electro-acoustic transducers 235 to meet some or all of the one or more performance parameters. In some embodiments, such analog and/or digital response shaping networks may be incorporated with and/or coupled to audio interface 230, amplification circuitry 240, audio bus 275, amplified audio bus 280, and/or calibrated electro-acoustic transducer 235. In some embodiments, calibrated tuning appliance 200 may also employ analog and/or digital response shaping networks when reproducing a pre-recorded sound file 260 to alter the reproduced frequency spectrum of the audio signal propagating in the air to suit a desired frequency spectrum.

Because electro-acoustic transducers 235 are calibrated to perform to a known standard, in various embodiments, calibrated tuning appliance 200 may be capable of consistently reproducing one or more pre-recorded sound files 260 (and/or custom-recorded sound files) such that propagated sound waves 140 in the air have frequency response, sound pressure level ("SPL"), and distortion characteristics within predetermined tolerances. Thus, different users may have a similar experience when similar sound files 260 are reproduced on different calibrated tuning appliances 200. Similarly, a user's calibrated tuning appliance 200 may provide a consistent tuning standard with little or no variation from tuning session to tuning session, reducing or eliminating inconsistencies such as variations in a human auditory healthcare professional's voice from session to session.

Figure 3:
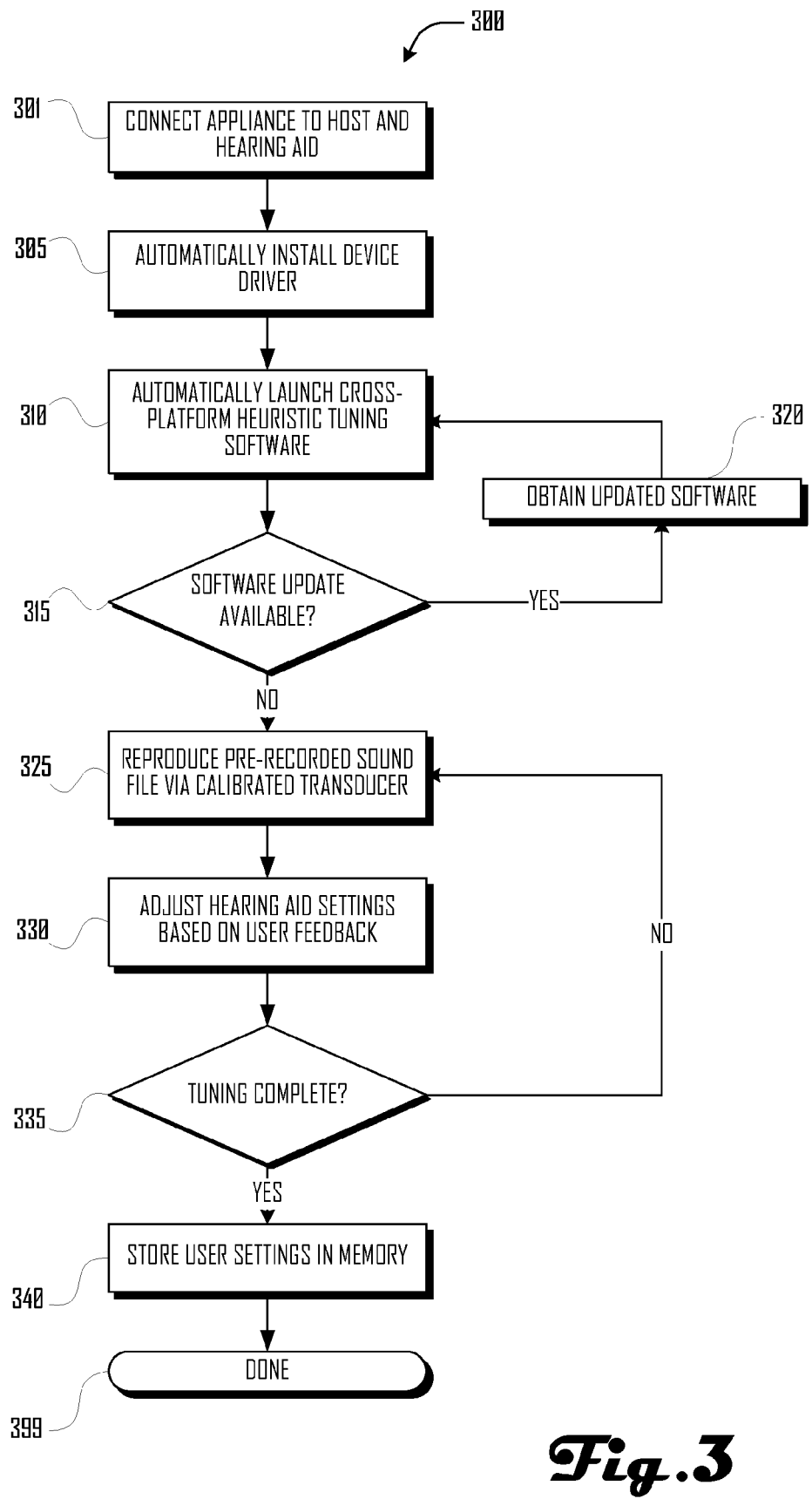
FIG. 3 is a flow diagram illustrating a calibrated tuning appliance tuning routine in accordance with one embodiment.

FIG. 3 is a flow diagram illustrating a calibrated tuning appliance tuning routine 300 in accordance with one embodiment. At block 301, a calibrated tuning appliance 200 is connected to a host 115 and to one or more hearing aids 130A-B. At block 305, a device driver 255 is automatically installed (if needed) at host 115, and at block 310, heuristic tuning routine 500 (see FIG. 5, discussed below) is automatically launched. At block 315, routine 300 determines whether a software update is available. If so, the updated software is obtained in block 320, stored in memory 250, and the updated heuristic tuning routine 500 is re-launched in block 310. When no more software updates are available, routine 300 proceeds to block 325, one or more pre-recorded sound files are audibly reproduced for the user via calibrated electroacoustic transducer 235. In block 330, the user's hearing aid settings are adjusted in accordance with feedback obtained from the hearing aid wearer 105. If additional tuning is desired, routine 300 repeats blocks 325-35 until tuning is complete. Once tuning is complete, the final set of hearing aid settings is stored in block 340 in user data 265 in memory 250. Routine 300 ends at block 399.

FIGS. 4-11 illustrate various alternate embodiments of heuristic hearing-aid tuning systems and methods.

Many hearing aids provide one or more adjustable audio processing controls (i.e., processing circuits and/or routines) that may be used to tune a hearing aid to compensate for a particular individual's distinct pattern of hearing loss. In various embodiments, a hearing aid may provide gain controls, such as compressor controls, limited controls, and the like, and one or more equalization filters, such as peaking equalization filters; high- and/or low-shelf filters; high-, low-, and/or band-pass filters; allpass filters; notch filters; and the like. In various embodiments, such controls may be implemented as passive and/or active controls; digital and/or analog controls; linear and/or non-linear controls; and the like. Moreover, in some embodiments, a hearing aid may provide one or more additional processing controls such as feedback suppression, noise reduction, and the like.

Figure 4:
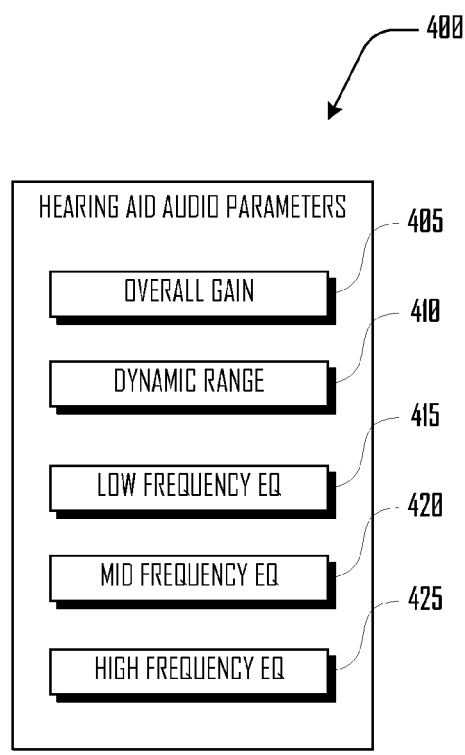
FIG. 4 lists an illustrative set of hearing aid audio tuning parameters in accordance with one embodiment.

FIG. 4 illustrates an exemplary set of adjustable hearing aid audio parameters 400. In various embodiments, a hearing aid may provide adjustable audio parameters 400 including some or all of the following: overall gain 405, dynamic range 410, low-frequency equalization 415, mid-frequency equalization 420, high-frequency equalization 425, and the like. In other embodiments, more or fewer parameters may be present. In some embodiments, some or all of the adjustable audio parameters 400 may comprise a plurality of adjustable audio sub-parameters. For example, dynamic range parameters 410 may include sub-parameters to control compressor and/or limiter settings such as threshold, attack time, release time, compression ratio, and the like.

Similarly, some or all of low-, mid-, and high-frequency equalization 415-25 parameters may comprise parameters controlling equalization within a plurality of sub-bands. For example, in one embodiment, low-frequency equalization parameters 415 may include gain and/or "Q" (bandwidth) parameters to control equalization filters centered at or near 150 Hz, 240 Hz, and 380 Hz; mid-frequency equalization parameters 420 may include gain and/or "Q" parameters to control equalization filters centered at or near 600 Hz, 950 Hz, and 1500 Hz; and high-frequency equalization parameters 425 may include gain and/or "Q" parameters to control equalization filters centered at or near 2.4 kHz, 3.8 kHz, and 6 kHz. In some embodiments, low-, mid-, and high-frequency equalization 415-25 parameters may also include parameters to control adjustable center frequencies, cutoff frequencies, and the like for equalization filters.

In some embodiments, a hearing aid may provide more or fewer bands of equalization compared to the illustrative embodiments disclosed above. In one embodiment, a hearing aid may provide a selectable number of equalization filters, in which case adjustable hearing aid audio parameters 400 may further include parameters to control the number of equalization filters. Similarly, in some embodiments, a hearing aid may provide a selectable equalization filter type, in which case, adjustable hearing aid audio parameters 400 may further include parameters to control one or more equalization filter types (e.g., high pass, low pass, peaking, shelving, and the like).

Figure 5:
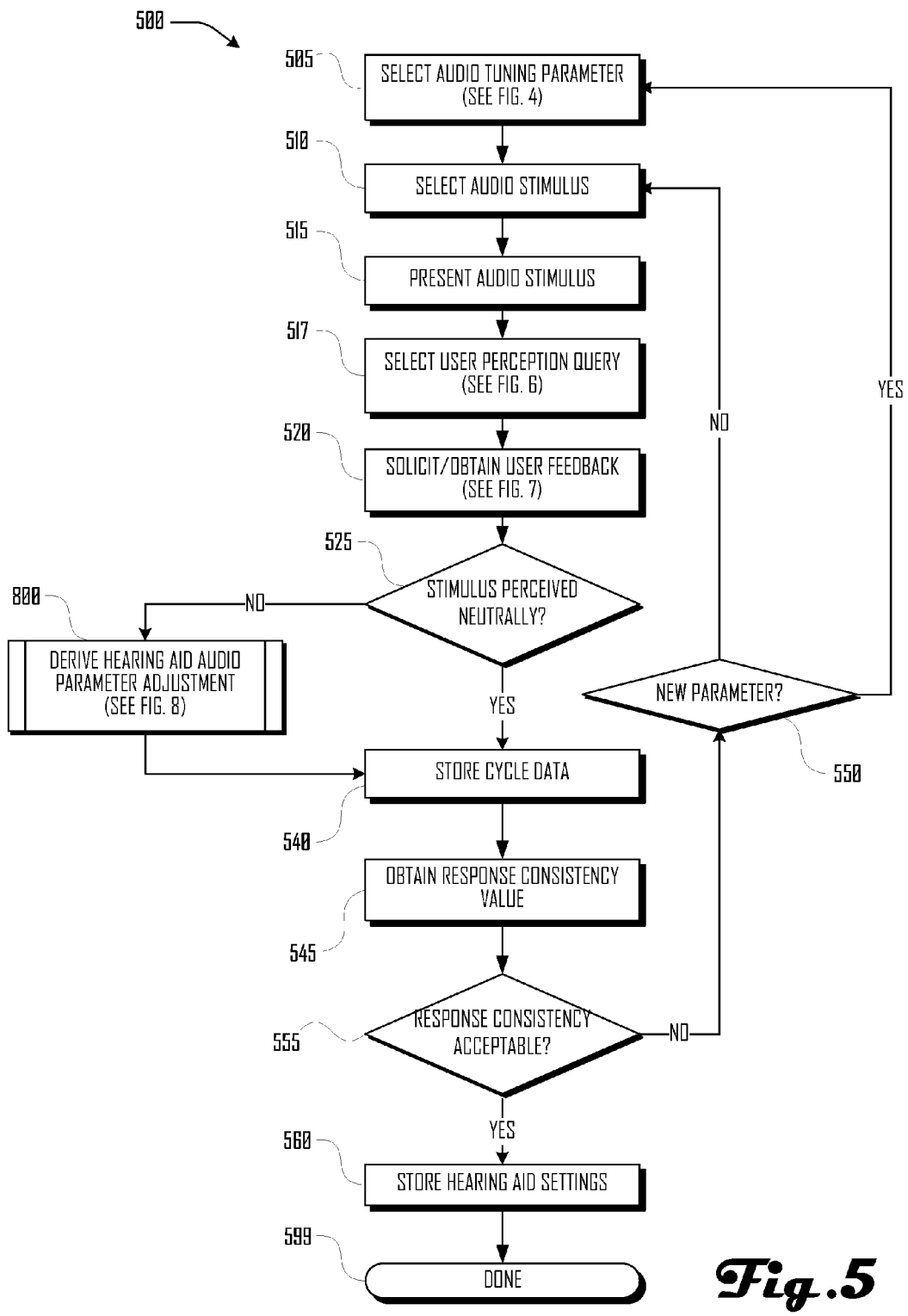
FIG. 5 is a flow diagram illustrating a heuristic hearing aid tuning routine in accordance with one embodiment.

FIG. 5 illustrates a heuristic hearing aid tuning routine 500 in accordance with one embodiment. Routine 500 iterates over one or more "tuning cycles" from block 505 to block 555. In some cases, routine 500 could be used, along with pure tone audio stimulus, to prepare an audiogram measuring a user's unaided hearing or hearing loss. However, in most cases, routine 500 is used to present audio stimulus to a user 105 while the user is wearing his or her hearing aids 130A-B, and while the user's hearing aids 130A-B are communicatively coupled to calibrated tuning appliance 200 so that adjustments can be made to the hearing aid settings in accordance with feedback from the user. Further aspects of various embodiments are described in U.S. patent application Ser. No. 12/760,431 entitled "HEARING AID TUNING METHOD", with inventors Daniel Wiggins and Donald Bowie, which is hereby fully incorporated by reference.

Once the user 105 has coupled his or her hearing aids 130A-B to calibrated tuning appliance 200, heuristic tuning routine 500 iteratively proceeds as described below.

In block 505, one or more adjustable audio parameters 400 are selected. The selected parameter or parameters may be adjusted over the course of an iterative tuning cycle. In one embodiment, adjustable audio parameters 400 may be selected first in a pre-determined order, and then once tuning cycles have been performed for each adjustable audio parameter 400, subsequent tuning cycles may chose a specific parameter or even randomly select a tuning parameter. For example, in one embodiment, the first five tuning cycles may select the following respective tuning parameters: overall gain 405, dynamic range 410, low-frequency equalization 415, mid-frequency equalization 420, and high-frequency equalization 425. In other embodiments, a different set of tuning parameters may be selected and/or selected in a different order from that described above. In some embodiments, only the first two tuning cycles may select tuning parameters in a predetermined order (e.g., overall gain 405, dynamic range 410), then the third and subsequent cycles may select tuning parameters randomly or according to other methods such as those discussed below.

In other embodiments, adjustable audio parameters 400 may be selected first in a pre-determined order, and then once tuning cycles have been performed for each adjustable audio parameter 400, subsequent tuning cycles may select a tuning parameter based at least in part on data gathered and/or user inputs provided in previous tuning cycles. For example, in one embodiment, tuning parameters for the first two or five tuning cycles may be selected as described above, and tuning parameters for the third or sixth and subsequent cycles may be selected to accord with areas that routine 500 has determined to be sub-optimal. For example, after a number of tuning cycles, a hearing aid wearer may continue to provide inconsistent responses to queries related to, for example, the upper-midrange, indicating that these frequency regions may remain inadequately tuned. In such a case, routine 500 may be more likely to select tuning parameters related to the upper-midrange frequency region.

In still further embodiments, a tuning parameter may be selected using a combination of the methods discussed above (i.e., subsequent parameters selected according to a random weighting based in part on data gathered in previous cycles) and/or using another method of selecting tuning parameters.

In block 510, routine 500 selects an audio stimulus. In one embodiment, an audio stimulus is selected from among pre-recorded sound files 260 stored in memory 250 of calibrated tuning appliance 200. In some embodiments, an audio stimulus is selected randomly from among some or all available audio stimuli. In other embodiments, some or all available audio stimuli are selected in a pre-determined order. In still other embodiments, a list of some or all available audio stimuli is randomly scrambled and the audio stimuli are selected in the order they appear in the scrambled list.

In some embodiments, audio stimuli may be selected based at least in part on the tuning parameter selected in block 505. For example, if the selected tuning parameter relates to a frequency range around 200 Hz-300 Hz, an audio stimulus may be selected to comprise a female voice with a fundamental frequency in the indicated range. Similarly, if the selected tuning parameter relates to a frequency range above 3 kHz-4 kHz, an audio stimulus may be selected to comprise a voice speaking words including sibilant consonants. In other words, in some embodiments, when the tuning parameter selected in block 505 relates to a particular frequency range, in block 510, routine 500 may select an audio stimulus having energy directed to that particular frequency range.

Conversely, in some embodiments, an audio tuning parameter may be selected based at least in part on the selected audio stimulus. (i.e., in some embodiments, block 510 may be performed before block 505, and the selection in block 505 may depend at least in part on the selection in block 510.). For example, an audio stimulus may be selected in block 510 that comprises a voice speaking two words that differ only according to a vowel sound (e.g., "soup" and "soap"), and a tuning parameter may be selected in block 505 that relates to the frequency region where the differences in the two vowel sounds manifest (e.g., around 300-600 Hz for the illustrative vowel sounds).

In block 515, the selected audio stimulus is presented to the user via sound waves 140 propagated through the air. In many embodiments, the selected audio stimulus may be presented via a calibrated audio output chain, such that the sound waves 140 that reach the user 105 have frequency response, sound pressure level, and/or distortion characteristics within predetermined acceptable limits. For example, In one embodiment, sound waves 140 presented to the user 105 may deviate from the selected audio stimulus no more than +/−3 dB in frequency response from 150 Hz-8 kHz at no less than 85-90 dB (SPL) (measured at the user 105) with no more than 3% total harmonic distortion ("THD"). In one embodiment, the selected audio stimulus is presented via audio components 230-40 of calibrated tuning appliance 200.

In some embodiments, the selected audio stimulus may optionally be filtered or equalized before being presented. For example, in some cases, routine 500 may purposely boost or cut a particular frequency range of the selected audio stimulus as a consistency check (i.e., routine 500 may induce a "shrill" or "thin" sound to determine whether the user 105 perceives the sound as being "shrill" or "thin," see FIG. 6 and block 545, discussed below).

In block 517, routine 500 selects a user perception query. In one embodiment, the user perception query is selected from a predetermined list of such queries. In some embodiments, the predetermined list of user perception queries may be derived from standard speech intelligibility tests, such as tests that involve presenting pairs of words that differ only by an initial, final, or intervocalic consonant, or by only a single vowel sound. In such embodiments, the user perception query is likely to be closely tied to the selected audio stimulus and the selected tuning parameter.

In other embodiments, the selected audio stimulus may comprise a 10-15 second long phrase or sentence, and the user perception query may be selected from a predetermined list of questions designed to elicit feedback about the user's subjective perception of sound waves 140 that propagate the selected audio stimulus through the air to the user 105.

Figure 6:
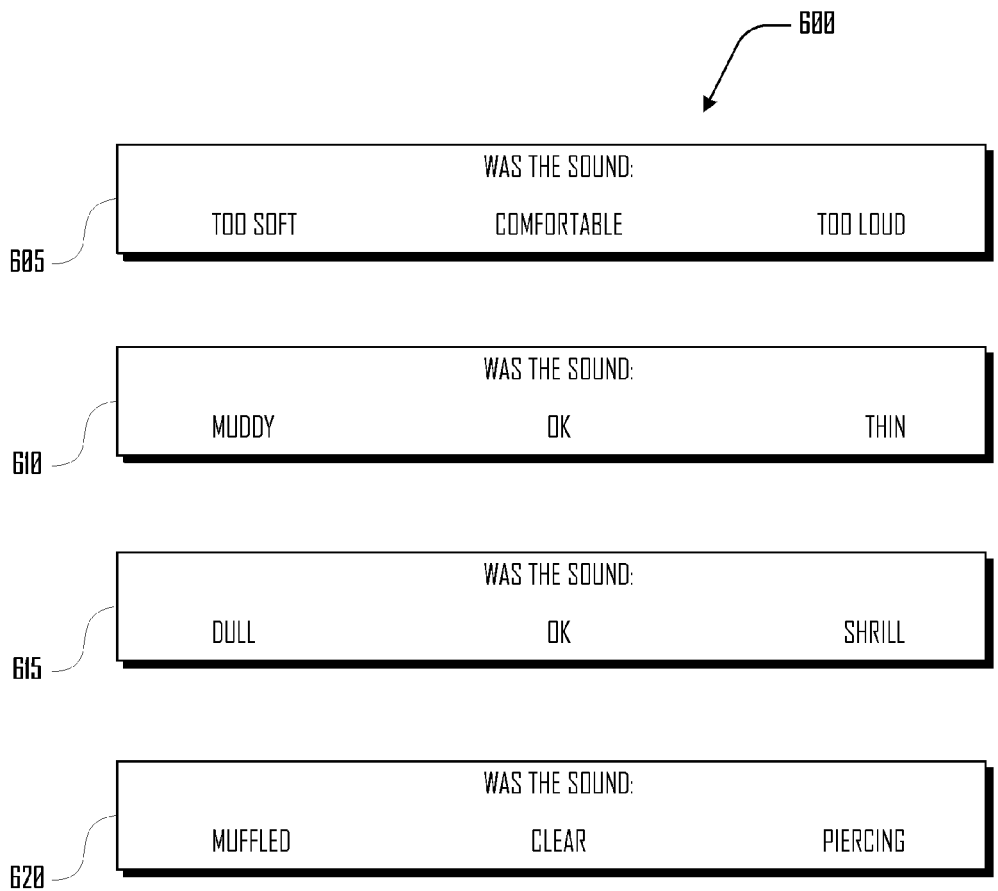
FIG. 6 illustrates several exemplary user perception queries in accordance with one embodiment.

In one embodiment, as illustrated in FIG. 6, user perception queries may take the form of "Goldilocks" questions, asking the user whether the audio stimulus he or she just perceived was at one end of a subjective spectrum, neutral, or at the other end of the subjective spectrum (i.e., was the sound "too hot," "just right," or "too cold").

Queries 605-20 illustrate several exemplary "Goldilocks" perception questions. Some embodiments will employ a greater number of queries than are illustrated in FIG. 6. Query 605 (too soft . . . comfortable . . . too loud) may be suitable when the tuning parameter selected in block 505 relates to the user's perception of the sound pressure level of the presented audio stimulus (e.g., overall gain 405, dynamic range 410, and the like). Queries 610-20 may elicit feedback related to the user's perception of the frequency spectrum of the presented audio stimulus, and queries 610-20 the may be suitable when the selected tuning parameter relates to a frequency range. In other embodiments, a user perception query may take other forms, such as asking the user to rate his or her perception of the presented audio stimulus along a range (e.g., 1-5, 1-10, and the like) or as a binary choice (e.g., good or bad).

Generally, non-neutral responses to a user perception query may be associated with one or more audio tuning parameters. For example, a "muddy" response may indicate that the user 105 perceives too much energy in the low frequency range or the midrange, depending on the spectral content of the presented audio stimulus (see FIG. 8, discussed below). Conversely, a "thin" response may indicate that the user 105 perceives too little energy in the low- and/or midrange, again depending on the spectral content of the presented audio stimulus. Similarly, a "shrill" response may indicate that the user 105 perceives too much energy in the high-frequency range. In some cases, different perception queries may overlap to some extent. For example, query 615 and query 620 may generally provide similar clues about the user's perception of the presented audio stimulus. In some embodiments, such redundancy may be desired because different users may associate different spectral imbalances with different terms, and/or different users may have divergent interpretations of the same term.

Referring again to FIG. 5, in block 520, feedback is solicited and obtained from the user 105. In one embodiment, feedback is solicited via a graphical display associated with host 115 and/or calibrated tuning appliance 200, and feedback is obtained via an input device associated with the same.

Figure 7:
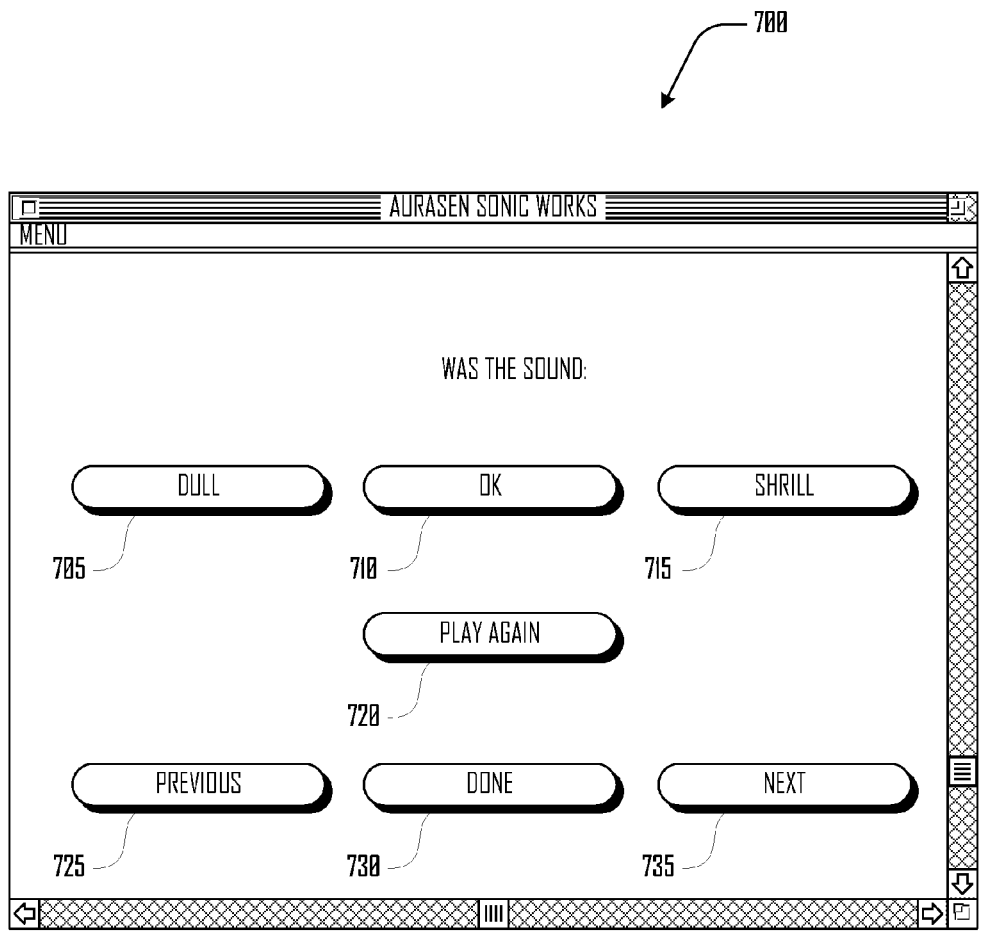
FIG. 7 is a diagram illustrating a user perception feedback input graphical user interface, in accordance with one embodiment.

For example, as illustrated in FIG. 7, the selected user perception query may be displayed on a display 700 with graphical user interface ("GUI") controls provided for the user to provide feedback. For example, in one embodiment, the user may click one of a plurality of buttons 705-15 to provide feedback on his or her subjective perception of the presented audio stimulus. In some embodiments, additional controls, such as some or all of controls 720-35, may also be provided via GUI display 700. In various embodiments, GUI controls may be displayed on a display 225 associated with calibrated tuning appliance 200 and/or host 115. Similarly, in various embodiments, input from the user 105 may be accepted via input device 220 and/or an input device associated with host 115.

Referring again to FIG. 5, in block 525, routine 500 determines whether the user-provided feedback was neutral or "just right" (e.g., "OK" 610). If user feedback was neutral, then the user likely did not perceive an imbalance from the sound he or she perceived. Therefore, in most cases, there is no need to adjust the selected tuning parameter when the user provides neutral feedback, so routine 500 proceeds to block 540, in which some or all of the following data related to the current cycle is stored at least temporarily: the user's feedback, the selected tuning parameter, the selected audio stimulus, current date and/or time, the number of times the user replayed the audio stimulus (if a replay control 720 is offered), the amount of time the user took to provide feedback, and the like.

If decision block 525 determines that the user did not provide neutral feedback in block 520, routine 500 derives one or more hearing aid audio parameter adjustments. In some cases, it may be relatively simple to map the selected user perception query onto an audio parameter adjustment. For example, when the selected audio tuning parameter relates to overall gain, and the user feedback indicates that the presented audio stimulus was "too loud" or "too soft," then the derived audio parameter adjustment may simply be to lower or raise a gain control by some increment, e.g., −3 dB or +3 dB, respectively. In such a case, routine 500 may translate the determined audio adjustment into one or more programming instructions and program the user's hearing aid(s) 130A-B to conform to the new settings.

In some embodiments, when overall gain is being tuned, a gain adjustment increment may be greater or smaller than 3 dB. In one embodiment, a gain adjustment increment may be relatively large, e.g. 6 dB-12 dB, during early tuning cycles and relatively smaller, e.g. 1 dB-3 dB, during later tuning cycles. In another embodiment, routine 500 may present the user with additional feedback controls that map to different gain adjustment increments. For example, the user may be able to indicate that the presented audio stimulus was "much too loud/soft," in which case a larger increment (e.g., 6 dB-12 dB) may be used, or merely "slightly too loud/soft," in which case a smaller increment (e.g., 1 dB-3 dB) may be used However, in many cases, it may be more difficult to map the selected user perception query onto an audio parameter adjustment. For example, when the selected audio tuning parameter relates to gain adjustments of a particular frequency range, routine 500 may invoke a subroutine such as subroutine 800, illustrated in FIG. 8 and discussed below, in which an adjustment to the selected audio tuning parameter may be derived from the user's feedback as it relates to the presented audio stimulus. Once a hearing aid audio parameter adjustment has been derived, routine 500 proceeds to block 540, as discussed above.

In block 545, routine may obtain a consistency value associated with data stored in block 540. In block 555, the obtained response consistency value is evaluated to determine whether to perform an additional tuning cycle. For example, the stored data may indicate that the user consistently finds presented stimuli to be too shrill, suggesting not only that subsequent tuning cycles may be desirable (i.e., routine 500 should proceed to block 550), but also that subsequent cycles may wish to emphasize high-frequency related tuning parameters. Conversely, the stored data may indicate that the user's responses (or the user's recent responses) generally conform to perceptions that are expected, considering the spectral content of the presented audio stimuli. In such cases, routine 500 may proceed to block 560, in which the user's final hearing aid settings may be persistently stored, along with some or all of the collected tuning cycle data. At block 599, routine 500 ends.

If decision block 555 determines that additional tuning cycles may be needed to improve the user's response consistency, routine 500 proceeds to decision block 550, in which routine 500 determines whether to select a new audio tuning parameter. In one embodiment, routine 500 generally devotes 2-4 tuning cycles to the same tuning parameter before selecting a new tuning parameter. In other embodiments, routine may determine whether to choose a new tuning parameter based at least in past on whether the user has recently provided consistent responses to the current tuning parameter. If a new audio tuning parameter is to be selected (in decision block 550), routine 500 iterates to block 505, where a new tuning cycle begins. If not, routine 500 iterates to block 510, where a new tuning cycle begins.

Figure 8:
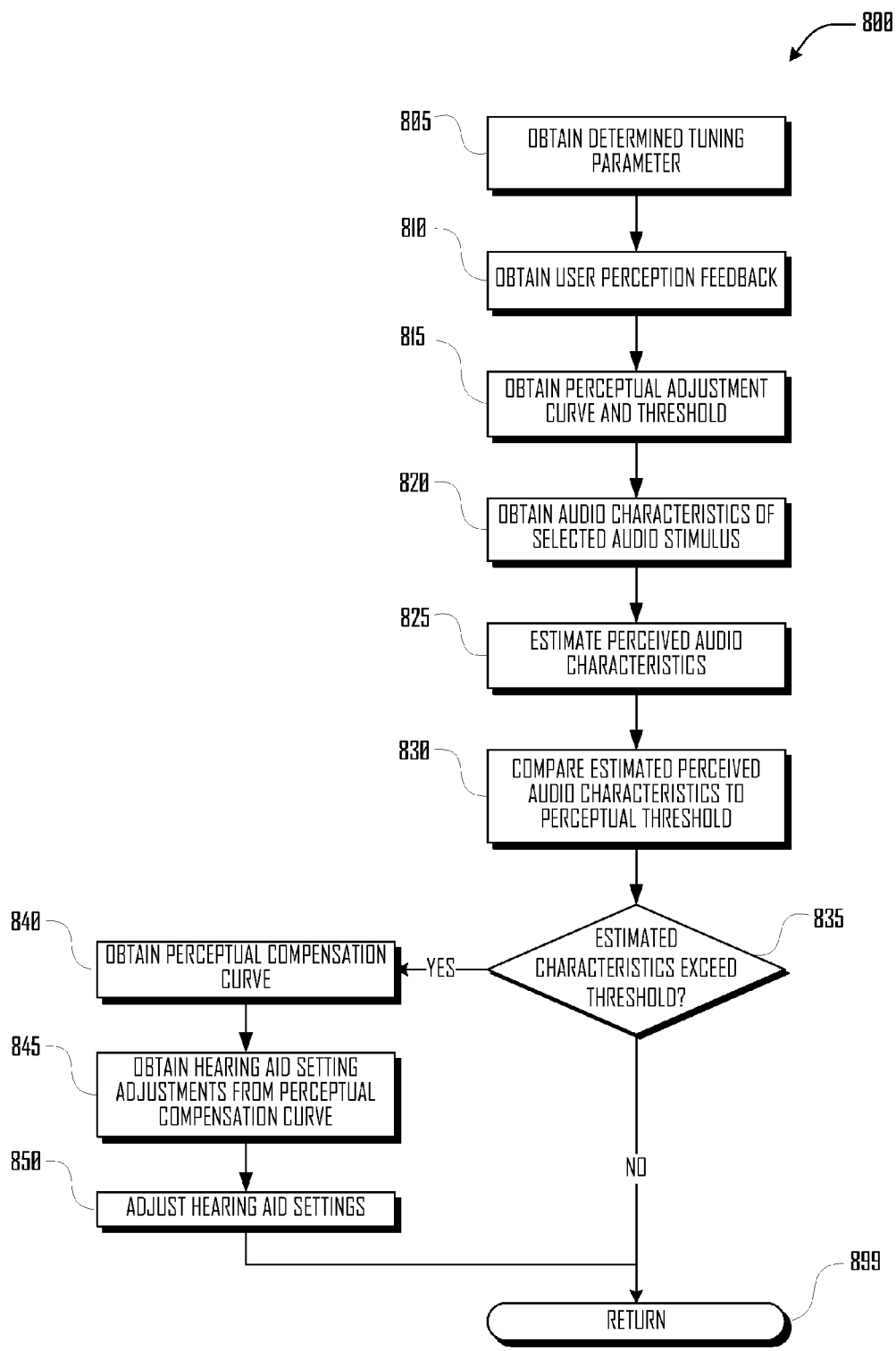
FIG. 8 is a flow diagram illustrating a hearing aid audio parameter adjustment subroutine in accordance with one embodiment.

FIG. 8 illustrates an exemplary hearing aid frequency-related audio parameter adjustment subroutine 800 in accordance with one embodiment. In block 805, routine 800 obtains a determined tuning parameter, such as the tuning parameter selected in block 505 of hearing aid tuning routine 500. In one embodiment, the determined audio tuning parameter may be associated with a frequency range. Similarly, in block 810, subroutine 800 obtains a user perception feedback, such as that obtained in block 520 of hearing aid tuning routine 500.

In block 815, subroutine 800 obtains a perceptual adjustment curve and threshold in accordance with the obtained user perception feedback. In some embodiments, perceptual thresholds may be weighted according to a subjective equal-loudness curve, such as A-weighting curves, C-weighting curves, Fletcher-Munson curves, Robinson-Dadson curves, and the like.

Figure 9:
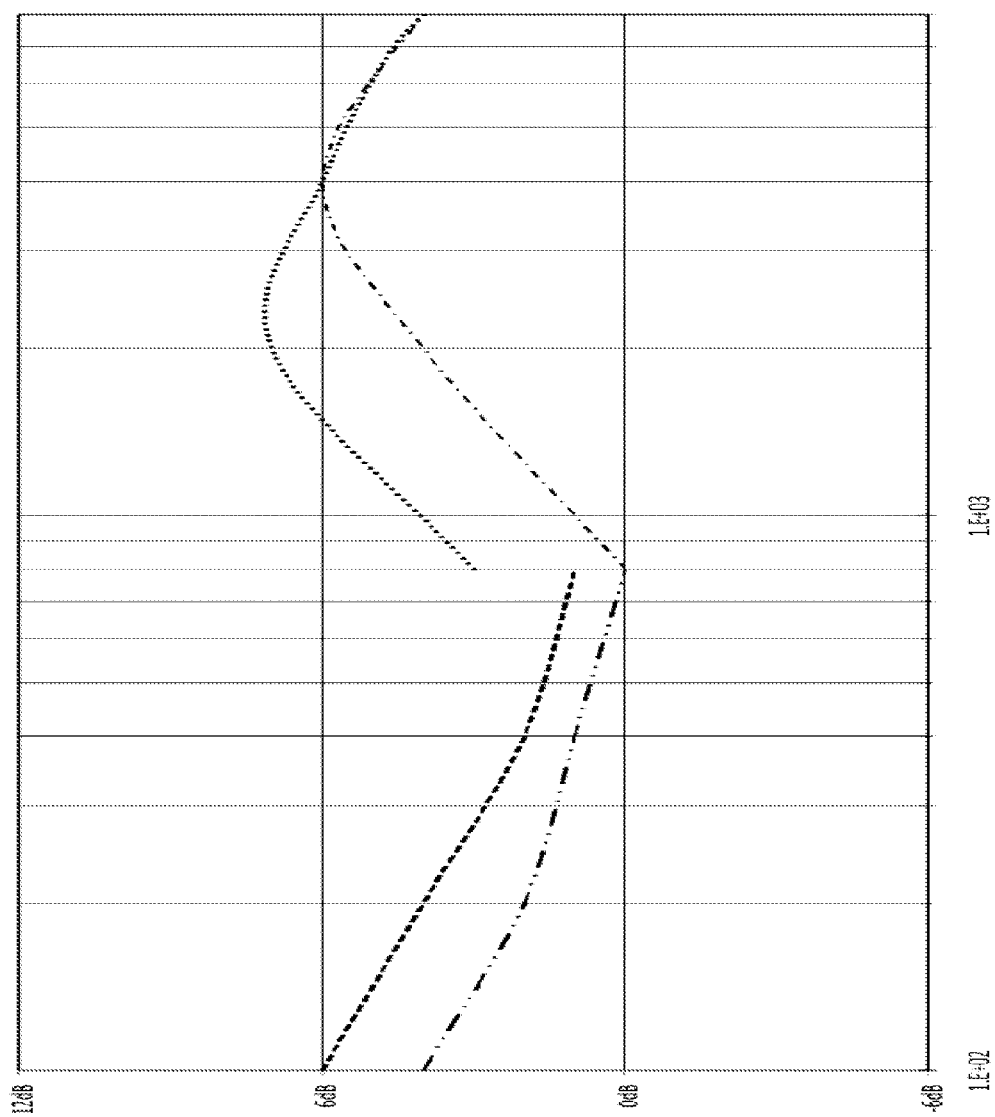
FIGS. 9-11 are normalized graphs plotting sound pressure level ("SPL") in decibels (y-axis) versus logarithmic frequency in hertz (x-axis) for various illustrative sets of data utilized by the perception evaluation subroutine of FIG. 8, in accordance with one embodiment.
Figure 10:
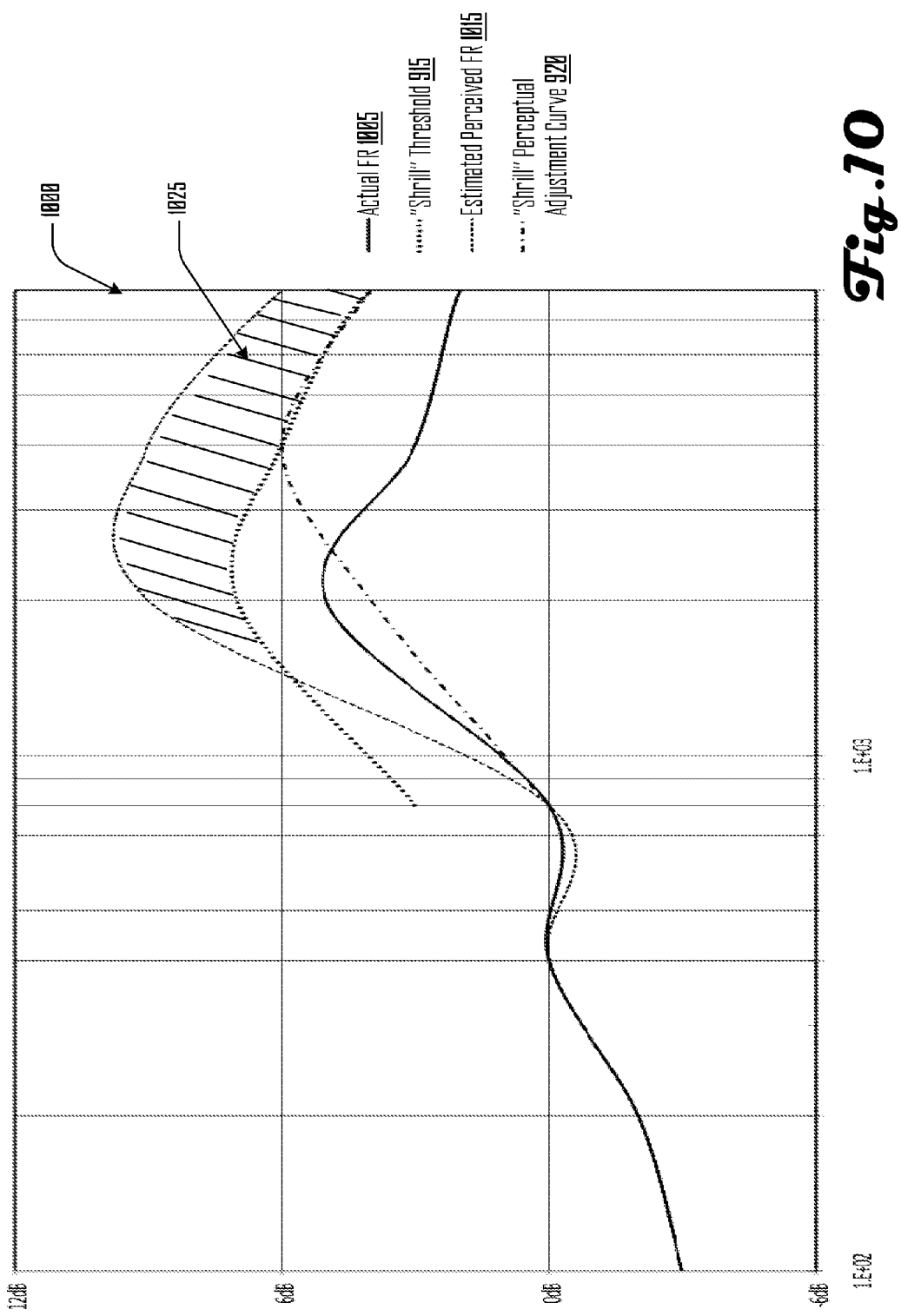
Figure 11:
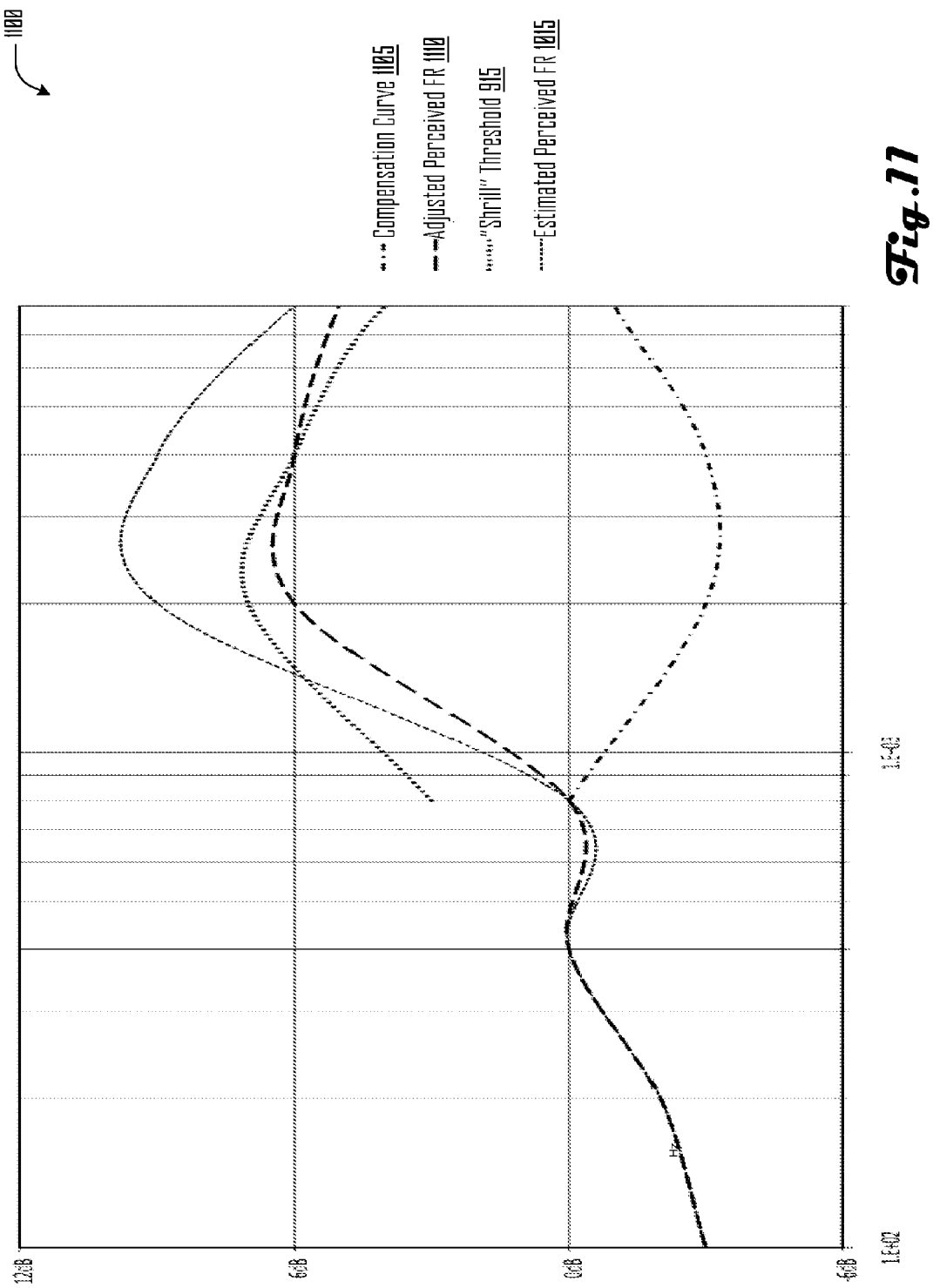

FIGS. 9-11 plot sound pressure level ("SPL") in decibels (y-axis) versus logarithmic frequency in hertz (x-axis) for various illustrative sets of data utilized by the perception evaluation subroutine of FIG. 8, in accordance with one embodiment FIG. 9 illustrates two exemplary sets of perceptual adjustment curves and thresholds. In various embodiments, a perceptual threshold, such as "Shrill" threshold 915 and "Muddy" threshold 905, may be used to determine at least in part whether to adjust a hearing aid setting in response to a particular user feedback for a particular presented audio stimulus. If a perceptual threshold determines that an adjustment is warranted, in various embodiments, a perceptual adjustment curve may be used to determine an appropriate audio parameter adjustment to make in response to a particular user feedback for a particular presented audio stimulus.

"Shrill" threshold 915 and "Muddy" threshold 905, like all lines of data depicted in FIGS. 9-11, are presented merely as aids to more clearly illustrate the concepts described herein—they do not necessarily represent actual data that may be employed in any particular embodiment, and they should not be construed to limit the scope of embodiments beyond the illustrative embodiments described below. Similarly, in some embodiments, the continuous lines of data depicted in FIGS. 9-11 may represent discrete data points that have been smoothly connected merely for illustrative purposes.

In one embodiment, a perceptual threshold comprises one or more frequency-specific or frequency-range-specific sound pressure level ("SPL") values. For example, the illustrative "Shrill" threshold 915 comprises a set of SPL values ranging from about 3 dB around 800 Hz, to about 7 dB around 2 kHz, to around 4 dB around 8 kHz. Similarly, "Muddy" threshold 905 comprises SPL values ranging from about 6 dB around 100 Hz, to about 2 dB around 800 Hz. For clarity, the illustrative thresholds 905, 915 (as well as frequency response ("FR") curves 1005, 1015, and 1110) are depicted with SPL values relative to an arbitrary 0 dB reference. In various embodiments, actual perceptual thresholds (and frequency response curves) may be relative to an objective 0 dB reference, such as 20 µPa (rms), or other standardized normal human hearing threshold.

Similarly, in various embodiments, perceptual adjustment curves may comprise one or more frequency-specific or frequency-range-specific adjustment values. For example, the illustrated "Shrill" perceptual adjustment curve 920 comprises adjustment values ranging from about 0 dB around 800 Hz, to about +6 dB around 4 kHz, to about +4 dB around 8 kHz. Similarly, the illustrative "Muddy" perceptual adjustment curve 910 ranges from about +4 dB around 100 Hz, to about 0 dB around 800 Hz. In various embodiments, as discussed further below, perceptual adjustment curves may be used to estimate the user's likely perception of a particular audio stimulus based on the user's feedback about that particular audio stimulus.

Referring again to FIG. 8, in block 820, subroutine 800 obtains audio characteristics of the selected audio stimulus. In various embodiments, such audio characteristics may comprise one or more frequency-specific or frequency-range-specific SPL values. In some embodiments, such audio characteristics may have been pre-determined and at least temporarily stored in an accessible memory. In other embodiments, such audio characteristics may be determined "on the fly," as needed. In some embodiments, such audio characteristics may be "normalized" to an arbitrary reference; in other embodiments, they may be relative to an objective measure of sound pressure. In some embodiments, such audio characteristics may be weighted according to a subjective equal-loudness curve, such as A-weighting curves, C-weighting curves, Fletcher-Munson curves, Robinson-Dadson curves, and the like.

In various embodiments, determining audio characteristics may include transforming audio data of an audio stimulus from the time domain into the frequency domain, according to any suitable method, and measuring the amount of energy present in one or more frequency bins. In other embodiments, determining audio characteristics may include passing an audio stimulus through a plurality of tuned resonant filters and measuring the amplitudes of the outputs of the plurality of resonant filters. In still other embodiments, determining audio characteristics may include analyzing an audio stimulus according to other methods, such as Linear Predictive Coding ("LPC") and the like.

FIG. 10 depicts in line 1005 (labeled "Actual FR") an illustrative set of audio characteristics of a hypothetical audio stimulus relative to an arbitrary 0 dB reference. As illustrated by audio characteristics line 1005, the hypothetical audio stimulus includes relatively more energy above 1 kHz than below 1 Hz.

Referring again to FIG. 8, in block 825, subroutine 800 modifies the audio characteristics obtained in block 820 according to the perceptual adjustment curve obtained in block 815. The resulting modified audio characteristics may estimate the user's perception of the presented audio stimulus. For example, in the scenario depicted in FIG. 10, the user provided feedback indicating that the presented audio stimulus was "Shrill." Line 1015 in FIG. 10 (labeled "Estimated Perceived FR") depicts the Actual FR 1005 of the presented audio stimulus modified by the "Shrill" perceptual adjustment curve 920. Line 1015 thus represents subroutine 800's estimate of the user's perception of the presented audio stimulus, as suggested by the user's feedback.

Referring again to FIG. 8, in block 830, subroutine 800 compares the estimated perceived audio characteristics (e.g., Estimated Perceived FR 1015) to the perceptual threshold obtained in block 815 (e.g., "Shrill" Threshold 915). In decision block 835, subroutine 800 determines whether all or part of the estimated perceived audio characteristics (e.g., Estimated Perceived FR 1015) exceeds the perceptual threshold (e.g., "Shrill" Threshold 915). For example, as illustrated in FIG. 10, shaded region 1025 depicts that Estimated Perceived FR 1015 exceeds "Shrill" Threshold 915 from around 1.5 kHz up to at least 8 kHz.

Referring again to FIG. 8, if decision block 835 determines that the estimated audio characteristics do not exceed the perception threshold, then the subroutine may proceed to return block 899 without adjusting the user's hearing aid settings. However, if decision block 835 determines that the estimated audio characteristics exceed the perception threshold, then the user's hearing aid settings may be adjusted in blocks 840-50, as discussed below.

Thus, in various embodiments, perceptual threshold curves may be used as a sort of "sanity test" to evaluate whether a particular user feedback provides meaningful information about the user's perception of a particular presented audio stimulus. For example, in some cases, the selected audio tuning parameter may relate to a high-frequency region, and a user may provide feedback that he or she perceived a particular audio stimulus as "shrill," feedback that generally indicates that the user is perceiving too much energy in one or more high-frequency regions. However, if the energy in the upper frequency ranges of that particular audio stimulus is below a "Shrill" perception threshold (not shown), then it may be unlikely that adjusting a high-frequency filter in the user's hearing aid would improve the user's perception. Accordingly, in some embodiments, the user's hearing aid(s) 130A-B may not be adjusted in the current tuning cycle.

If decision block 835 determines that the estimated audio characteristics exceed the perception threshold, routine 800 proceeds to block 840, which obtains a perceptual compensation curve associated with the selected user perception feedback. An illustrative perceptual compensation curve associated with "Shrill" feedback is depicted by line 1105 in FIG. 11, labeled "Compensation Curve." In various embodiments, perceptual compensation curves may comprise one or more frequency-specific or frequency-range-specific compensation values. For example, the illustrated "Shrill" perceptual compensation curve 1105 comprises compensation values ranging from about 0 dB around 800 Hz, to about −3 dB around 3 kHz, to about −1 dB around 8 kHz.

Referring again to FIG. 8, in block 845, routine 800 obtains one or more hearing aid setting adjustments in accordance with the obtained perceptual compensation curve and with the determined tuning parameter or parameters obtained in block 805. For example, referring to FIG. 11, the illustrative compensation curve 1105 may indicate that the gain of a hearing aid peaking filter centered around about 3 kHz should be reduced by around 3 dB, which the gain of a hearing aid filter centered around about 6 kHz should be reduced by about 2 dB. Similarly, if a determined tuning parameter is associated with a high-shelf filter, the illustrative compensation curve 1105 may indicate that the gain of a hearing aid high-shelf filter should be reduced by around 1-3 dB, depending on the filter's cutoff frequency.

In some embodiments, the obtained perceptual compensation curve may be used not only to determine a gain adjustment for a hearing aid filter, but it may also be used to determine other parameter settings for one or more hearing aid filters. For example, in one embodiment, compensation curve 1105 may indicate that the user's hearing aid(s) 130A-B may be programmed to implement a low-Q peaking filter (e.g., having a bandwidth of 2-3 octaves) centered at around 3 kHz with a gain of around −3 dB.

Referring again to FIG. 8, in block 850, routine 800 sends programming instructions to the user's hearing aid(s) 130A-B in accordance with the obtained compensation adjustments. Line 1110 in FIG. 11 depicts an estimate of how the user 105 may perceive the audio stimulus after the hearing aid implements the programming instructions. Line 1110 depicts that the user's estimated perception may still exceed the "Shrill" threshold 915 above around 4 kHz. However, in many embodiments, subroutine 800 does not attempt to completely compensate for any particular perception anomaly. Rather, due to the iterative nature of hearing aid tuning routine 500, the compensation adjustments made during any one tuning cycle may make only a relatively modest adjustment to the hearing aid's audio control settings. However, over several tuning cycle iterations, a user's hearing aid(s) 130A-B may become increasingly effective at compensating for the user's particular pattern of hearing loss.

Although specific embodiments have been illustrated and described herein, it will be appreciated by those of ordinary skill in the art that a whole variety of alternate and/or equivalent implementations may be substituted for the specific embodiments shown and described without departing from the scope of the present invention. This application is intended to cover any adaptations or variations of the embodiments discussed herein including the possibility of different adjustments to each hearing aid where more than one hearing aid is utilized.

The invention claimed is:

1. A computer-implemented heuristic method for tuning a hearing aid worn by a user, the method comprising:
    selecting, by the computer, an adjustable audio parameter from a plurality of adjustable audio parameters for tuning the hearing aid;
    selecting, by the computer, an audio stimulus having audio energy characteristics related to said adjustable audio parameter;
    presenting, by a calibrated audio output device associated with the computer, said audio stimulus to the user via sound waves propagated through the air and amplified by the hearing aid;
    selecting, by the computer, a user perception query, associated with said adjustable audio parameter, from a plurality of user perception queries;
    obtaining, by the computer, a user perception feedback value according to said user perception query, said user perception feedback value indicating that said audio stimulus was not perceived neutrally by the user;
    determining, by the computer, a perceptual adjustment curve and a threshold curve according to said user perception feedback value;
    adjusting, by the computer, said audio energy characteristics according to said perceptual adjustment curve to obtain an estimated perception curve that estimates the user's perception of said audio stimulus;
    determining, by the computer, whether at least a portion of said estimated perception curve exceeds said threshold curve; and
    when at least said portion of said estimated perception curve exceeds said threshold curve:
        determining, by the computer, at least one adjustment value for adjusting said adjustable audio parameter according to said user perception feedback value;
        programmatically coupling the computer to the hearing aid; and
        programming, by the computer, the hearing aid to adjust said adjustable audio parameter according to said at least one adjustment value.

2. The method of claim 1, wherein determining said at least one adjustment value for adjusting said adjustable audio parameter according to said user perception feedback value comprises:
    obtaining a perceptual compensation curve associated with said user perception feedback value; and
    determining said at least one adjustment value according to said perceptual compensation curve.

3. The method of claim 1, wherein:
    said plurality of adjustable audio parameters comprises a sequence of adjustable audio parameters;
    a previous adjustable audio parameter had been selected from said sequence of adjustable audio parameters during a previous tuning cycle; and
    selecting said adjustable audio parameter for tuning the hearing aid comprises selecting a next adjustable audio parameter from said sequence of adjustable audio parameters.

4. The method of claim 1, wherein selecting said adjustable audio parameter for tuning the hearing aid comprises selecting a random adjustable audio parameter from said plurality of adjustable audio parameters.

5. The method of claim 1, wherein said plurality of adjustable audio parameters comprises a dynamic range parameter, a low-frequency equalization parameter, a mid-frequency equalization parameter, and a high-frequency equalization parameter.

6. The method of claim 1, further comprising determining a consistency value according to said user perception feedback value and at least one previous user perception feedback value obtained during at least one previous tuning cycle.

7. The method of claim 6, further comprising:
    determining, according to said consistency value, that the user's perceptions related to said adjustable audio parameter are consistently non-neutral;
    performing a subsequent tuning cycle; and
    during said subsequent tuning cycle, selecting said adjustable audio parameter from said plurality of adjustable audio parameters.

8. The method of claim 7, further comprising, during said subsequent tuning cycle:
    determining, according to said consistency value, that the user's perceptions related to said adjustable audio parameter are consistently neutral;
    performing a subsequent tuning cycle; and
    during said subsequent tuning cycle, selecting a second adjustable audio parameter from said plurality of adjustable audio parameters.

9. A computer-readable, non-transitory storage medium having stored thereon instructions that, when executed by a processor, configure the processor to:
    select an adjustable audio parameter from a plurality of adjustable audio parameters for tuning the hearing aid;

select an audio stimulus having audio energy characteristics related to said adjustable audio parameter;

present, by a calibrated audio output device associated with the processor, said audio stimulus to the user via sound waves propagated through the air and amplified by the hearing aid;

select a user perception query, associated with said adjustable audio parameter, from a plurality of user perception queries;

obtain a user perception feedback value according to said user perception query, said user perception feedback value indicating that said audio stimulus was not perceived neutrally by the user;

determine a perceptual adjustment curve and a threshold curve according to said user perception feedback value;

adjust said audio energy characteristics according to said perceptual adjustment curve to obtain an estimated perception curve that estimates the user's perception of said audio stimulus;

determine whether at least a portion of said estimated perception curve exceeds said threshold curve; and when at least said portion of said estimated perception curve exceeds said threshold curve:

determine at least one adjustment value for adjusting said adjustable audio parameter according to said user perception feedback value;

programmatically couple the processor to the hearing aid; and program the hearing aid to adjust said adjustable audio parameter according to said at least one adjustment value.

10. The non-transitory storage medium of claim 9, wherein the instructions that configure the processor to determine said at least one adjustment value for adjusting said adjustable audio parameter according to said user perception feedback value further comprise instructions configuring the processor to:

obtain a perceptual compensation curve associated with said user perception feedback value; and determine said at least one adjustment value according to said perceptual compensation curve.

11. The non-transitory storage medium of claim 9, wherein:

said plurality of adjustable audio parameters comprises a sequence of adjustable audio parameters;

a previous adjustable audio parameter had been selected from said sequence of adjustable audio parameters during a previous tune cycle; and selecting said adjustable audio parameter for tuning the hearing aid comprises selecting a next adjustable audio parameter from said sequence of adjustable audio parameters.

12. The non-transitory storage medium of claim 9, wherein the instructions that configure the processor to select said adjustable audio parameter for tuning the hearing aid further comprise instructions configuring the processor to select a random adjustable audio parameter from said plurality of adjustable audio parameters.

13. The non-transitory storage medium of claim 9, wherein said plurality of adjustable audio parameters comprise a dynamic range parameter, a low-frequency equalization parameter, a mid-frequency equalization parameter, and a high-frequency equalization parameter.

14. The non-transitory storage medium of claim 9, wherein the memory stores further instructions that further configure the processor to determine a consistency value according to said user perception feedback value and at least one previous user perception feedback value obtained during at least one previous tuning cycle.

15. A computing apparatus for tuning a hearing aid worn by a user, the apparatus comprising a processor and a memory storing instructions that, when executed by the processor, configure the apparatus to:

select an adjustable audio parameter from a plurality of adjustable audio parameters for tuning the hearing aid;

select an audio stimulus having audio energy characteristics related to said adjustable audio parameter;

present, by a calibrated audio output device associated with the apparatus, said audio stimulus to the user via sound waves propagated through the air and amplified by the hearing aid;

select a user perception query, associated with said adjustable audio parameter, from a plurality of user perception queries;

obtain a user perception feedback value according to said user perception query, said user perception feedback value indicating that said audio stimulus was not perceived neutrally by the user;

determine a perceptual adjustment curve and a threshold curve according to said user perception feedback value;

adjust said audio energy characteristics according to said perceptual adjustment curve to obtain an estimated perception curve that estimates the user's perception of said audio stimulus;

determine whether at least a portion of said estimated perception curve exceeds said threshold curve; and when at least said portion of said estimated perception curve exceeds said threshold curve:

determine at least one adjustment value for adjusting said adjustable audio parameter according to said user perception feedback value;

programmatically couple the apparatus to the hearing aid; and program the hearing aid to adjust said adjustable audio parameter according to said at least one adjustment value.

16. The apparatus of claim 15, wherein the instructions that configure the apparatus to determine said at least one adjustment value for adjusting said adjustable audio parameter according to said user perception feedback value further comprise instructions configuring the apparatus to:

obtain a perceptual compensation curve associated with said user perception feedback value; and determine said at least one adjustment value according to said perceptual compensation curve.

17. The apparatus of claim 15, wherein:

said plurality of adjustable audio parameters comprises a sequence of adjustable audio parameters;

a previous adjustable audio parameter had been selected from said sequence of adjustable audio parameters during a previous tune cycle; and selecting said adjustable audio parameter for tuning the hearing aid comprises selecting a next adjustable audio parameter from said sequence of adjustable audio parameters.

18. The apparatus of claim 15, wherein the instructions that configure the apparatus to select said adjustable audio parameter for tuning the hearing aid further comprise instructions configuring the apparatus to select a random adjustable audio parameter from said plurality of adjustable audio parameters.

19. The apparatus of claim 15, wherein said plurality of adjustable audio parameters comprise a dynamic range parameter, a low-frequency equalization parameter, a mid-frequency equalization parameter, and a high-frequency equalization parameter.

20. The apparatus of claim 15, wherein the memory stores further instructions that further configure the apparatus to determine a consistency value according to said user perception feedback value and at least one previous user perception feedback value obtained during at least one previous tuning cycle.

* * * * *

UNITED STATES PATENT AND TRADEMARK OFFICE
CERTIFICATE OF CORRECTION

| | | |
|---|---|---|
| PATENT NO. | : 8,867,764 B1 | Page 1 of 1 |
| APPLICATION NO. | : 13/889217 | |
| DATED | : October 21, 2014 | |
| INVENTOR(S) | : Dan Wiggins et al. | |

It is certified that error appears in the above-identified patent and that said Letters Patent is hereby corrected as shown below:

On the Title Page, item (54) and in the Specification, column 1, for the title of the invention, Delete "CALIBRATED HEARING AID TUNING APPLIANCE" and insert -- HEURISTIC HEARING AID TUNING SYSTEM AND METHOD --, therefor.

Signed and Sealed this
Twenty-fourth Day of March, 2015

Michelle K. Lee
*Director of the United States Patent and Trademark Office*